(12) United States Patent
Simrell

(10) Patent No.: US 11,930,862 B2
(45) Date of Patent: Mar. 19, 2024

(54) MOUTHPIECE WITH ADJUSTMENT

(71) Applicant: Simrell Collection, LLC, Toledo, OH (US)

(72) Inventor: Austyn Simrell, Toledo, OH (US)

(73) Assignee: SIMRELL COLLECTION, LLC, Curtice, OH (US)

(*) Notice: Subject to any disclaimer, the term of this patent is extended or adjusted under 35 U.S.C. 154(b) by 344 days.

(21) Appl. No.: 17/320,842

(22) Filed: May 14, 2021

(65) Prior Publication Data

US 2021/0352960 A1    Nov. 18, 2021

Related U.S. Application Data

(60) Provisional application No. 63/025,532, filed on May 15, 2020.

(51) Int. Cl.
*A24F 7/00* (2006.01)
*A24F 40/70* (2020.01)
*A61M 15/00* (2006.01)

(52) U.S. Cl.
CPC ................ *A24F 7/00* (2013.01); *A24F 40/70* (2020.01); *A61M 15/0021* (2014.02); *A61M 2205/36* (2013.01); *A61M 2205/8206* (2013.01)

(58) Field of Classification Search
CPC ............ A24F 7/00; A24F 7/02; A61M 15/002
See application file for complete search history.

(56) References Cited

U.S. PATENT DOCUMENTS

| | | | | |
|---|---|---|---|---|
| 1,721,438 A | * | 7/1929 | Easton | A24F 13/10 131/182 |
| 2018/0110259 A1 | * | 4/2018 | Kartashov | A24F 1/22 |
| 2018/0228216 A1 | * | 8/2018 | Saygili | A24B 15/167 |

FOREIGN PATENT DOCUMENTS

| | | | | |
|---|---|---|---|---|
| CN | 113226417 A | * | 8/2021 | A24F 40/42 |
| KR | 10-1820841 B1 | * | 1/2018 | A24B 15/16 |
| TW | 201434404 A | * | 9/2014 | A24F 40/40 |

OTHER PUBLICATIONS

Translation of CN 113236417A (Year: 2021).*

* cited by examiner

*Primary Examiner* — Cynthia Szewczyk
(74) *Attorney, Agent, or Firm* — Michael E. Dockins; Shumaker, Loop & Kendrick, LLP

(57) ABSTRACT

A mouthpiece assembly for use with a vaporizer device includes a mouthpiece having an opening formed axially therethrough from a first end to an opposing second end thereof and an inner tubular member configured to be slidably received within the opening of the mouthpiece. A sliding of the inner tubular member within the opening of the mouthpiece changes an axial length of the mouthpiece assembly to allow for the mouthpiece assembly to be coupled to a variety of different outer tubular members of differing axial lengths that are compatible for use with the mouthpiece assembly for forming the resulting vaporizer device.

17 Claims, 5 Drawing Sheets

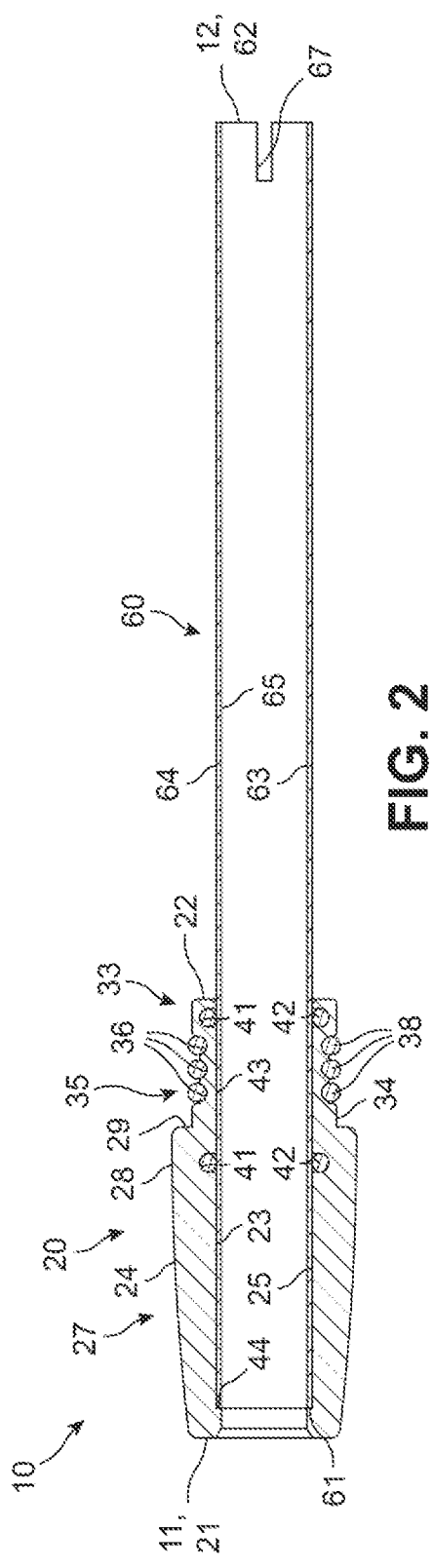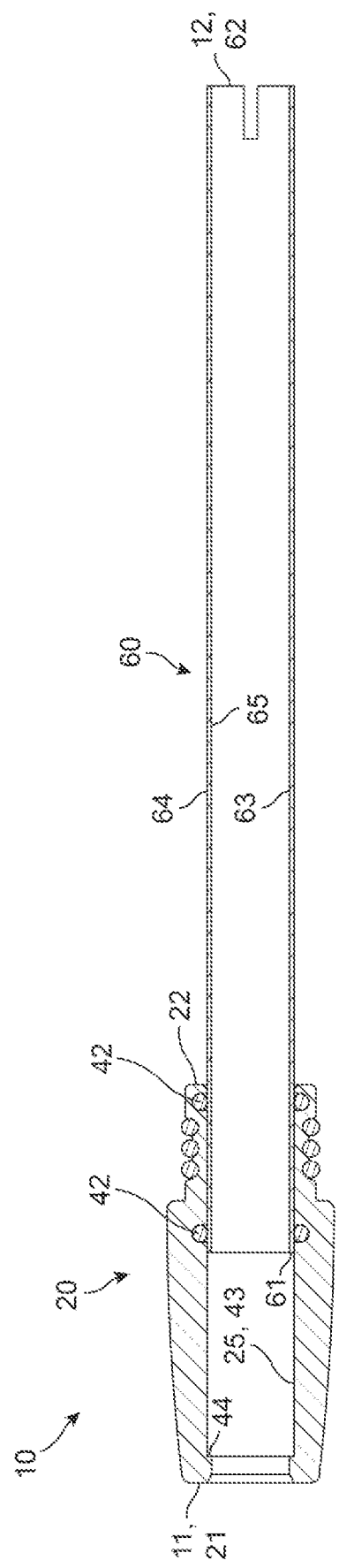

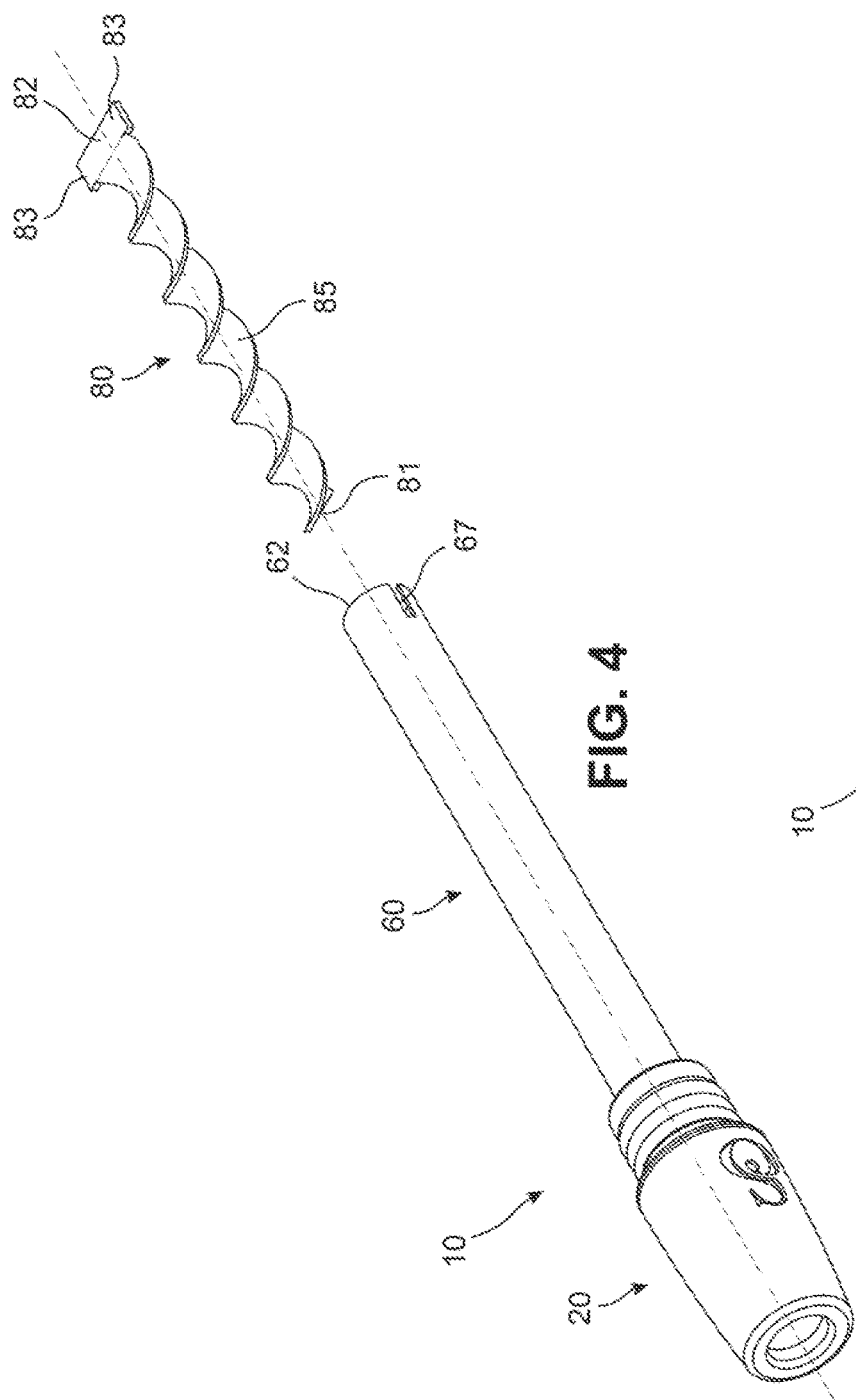
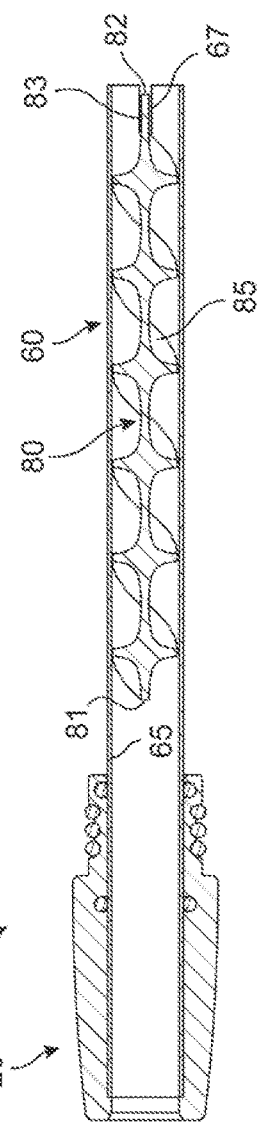

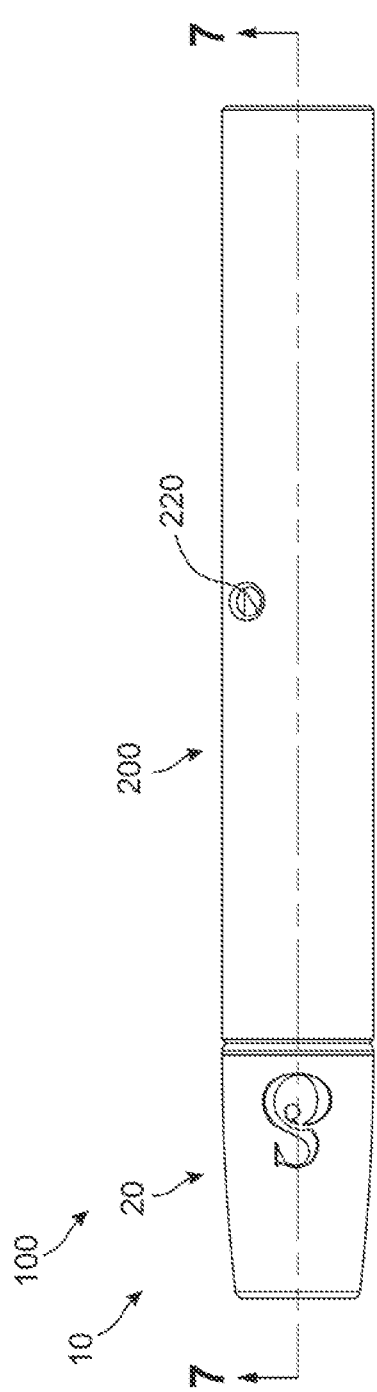
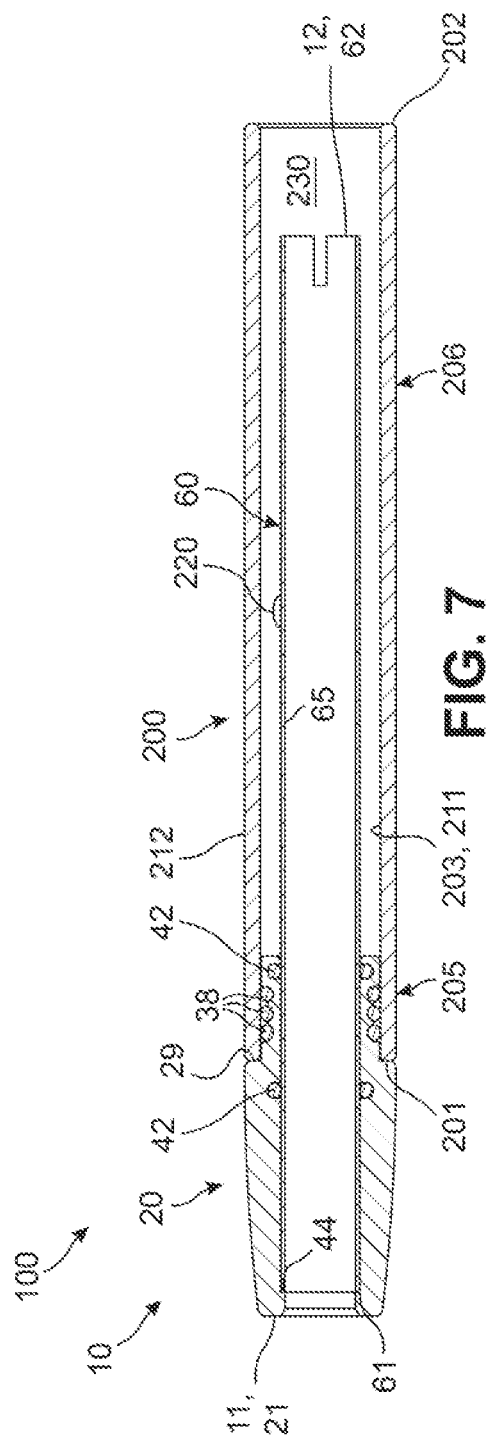

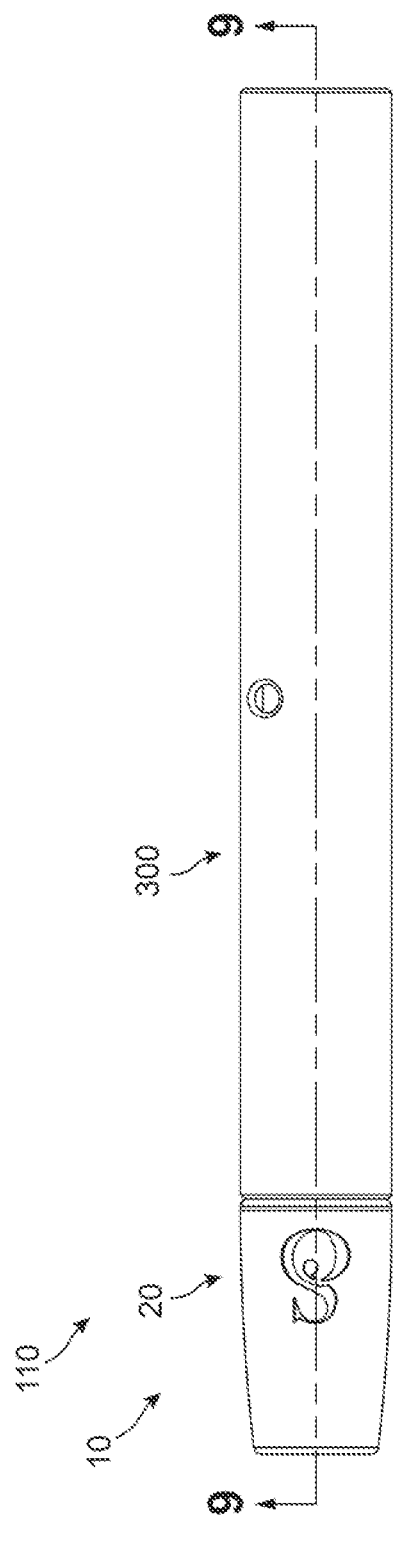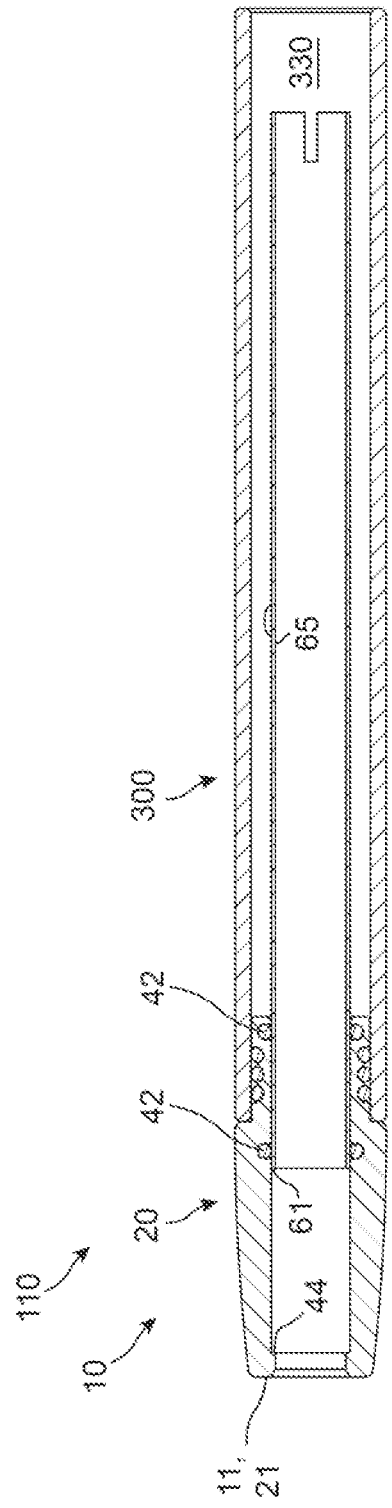

MOUTHPIECE WITH ADJUSTMENT

CROSS-REFERENCE TO RELATED APPLICATIONS

This application claims the benefit of U.S. Provisional Application No. 63/025,532 filed on May 15, 2020, the entire disclosure of which is hereby incorporated herein by reference.

FIELD

The present technology relates to the field of vaporizer cooling systems, and more specifically, to a vaporizer assembly having modular components for use with an external heating source.

INTRODUCTION

This section provides background information related to the present disclosure which is not necessarily prior art.

Various inhalation devices or vaporizers include implements for aerosolizing or vaporizing various substances for introduction into the respiratory system. Inhaled substances can be recreational or therapeutic in nature and can include certain natural, isolated, and/or synthetic substances. Examples of vaporized substances include certain plant materials, such as tobacco, cannabis, or other herbs or blends of essential oils. Vaporized substances can be combined with various vehicles, compounds, flavorings, etc., such as propylene glycol, glycerin, nicotine (e.g., extracted from tobacco), and provided in various liquid solutions. Use of a vaporizer is sometimes colloquially known as the act of "vaping" and the vaporizer device itself can be referred to as a "vape."

Vaporizers can be configured with different types of extraction chambers, including those having a straight bore, venturi, or sequential venturi, and can employ various materials, including heat resistant materials, such as metal or glass. Extracted vapor can be collected in various types of chambers or inhaled directly through a conduit. Certain vaporizers can provide extracted vapor at cooler temperatures than obtained by traditional smoking, which can be due at least in part to the absence of combustion as found in a smoking material, such as tobacco, and can result in more efficient extraction of desired compounds from the vaporized material. Hence, certain irritating and undesirable effects attributable to smoking can be reduced or minimized by vaping, including secondhand smoke.

An electronic cigarette, also referred to as an e-cigarette, is one type of a handheld battery-powered vaporizer that can simulate smoking by providing some of the behavioral aspects of smoking, including the hand-to-mouth action of smoking, but without combusting tobacco. Instead of cigarette smoke generated from combustion, the user or vaper inhales an aerosol, commonly called vapor. E-cigarettes can include a heating element that atomizes a liquid solution called e-liquid to form the vapor. Certain e-cigarettes are automatically activated by the user inhaling or drawing breath therethrough, while other e-cigarettes can turn on manually; e.g., by pressing a button. E-cigarettes can take many forms, can have an appearance like traditional cigarettes, can be reusable by replacement of vapor cartridges and batteries, for example, although certain e-cigarettes can be designed to be disposable.

Various types of vaporizers, including e-cigarettes, are increasing in popularity in recent years. As consumers become more aware of health consequences of inhaling smoke produced by combusting tobacco and other substances, vaporizers are seen as a better alternative to cigarettes, cigars, pipes, and other smoking implements. While some vaporizers are large and bulky—sometimes intended to mimic the aesthetic look of a hookah—most vaporizers are small enough to fit into a user's pocket or purse for convenience. However, known vaporizers can have certain drawbacks, including excess heat within the vapor to be inhaled, for example, when the vapor arrises from an external heat source such as an electronic heating element. Traditional smoking devices have mitigated heat from inhaled smoke by passing the smoke through conduits of increased length and/or passing the smoke through various heat sinks, including water reservoirs. Such means for reducing the temperature of inhaled smoke or vapor can unfortunately present difficulties in cleaning and sanitizing and can be difficult to customize to a user's preferences with respect to heat abatement.

Various types of vaporizers include a modular configuration wherein certain components forming the vaporizer assembly can be replaced interchangeably due to the common and substantially standard dimensions utilized in forming the coupling features of such components. Specifically, many vaporizer devices include components such as a mouthpiece, a heat exchanging feature, a casing forming a vapor extraction chamber, a battery, and a heating element which may be removable for cleaning and maintenance, or may be provided with the intention of such components being interchangeably installed into a vaporizer device for the purpose of customizing the vaporizer device and the associated vaping experience. This customization may be necessary to attain a desired flow configuration, temperature, and pressure of the inhaled vapor in accordance with the desires of the user. The customization can include installing certain components into a vaporizer device that is manufactured and sold as a unit, wherein the installation results in the addition of a new component (such as a heat exchanging feature) or the replacement of a corresponding component provided in the initially manufactured unit. The customization can alternatively include the purchase of several independent components that are subsequently assembled into a desired vaporizer device configuration.

However, it has been discovered that such customization is often limited by the interconnecting components having variable dimensions and configurations that are incompatible with each other, despite certain portions of the components having structure suitable for connecting the components in a desirable manner. For example, certain components such as the described heat exchanging feature may not be dimensioned for reception within certain casings and/or extraction chambers, or may interfere with or encroach upon adjacent components of the vaporizer device, such as the heating element or battery of the vaporizer device.

Accordingly, there is a need for an adjustable heat exchanging feature for use in vaporizer devices, wherein the adjustable heat exchanging feature is configured to be adjustable to accommodate the installation of the adjustable heat exchanging feature into a variety of different complimentary structures for forming a desired vaporizer device.

SUMMARY

The present technology includes articles of manufacture, systems, and processes that relate to a vaporizer assembly, including a mouthpiece assembly having an adjustable heating exchanging structure.

In one embodiment of the present invention, a mouthpiece assembly for use with a vaporizer device includes a mouthpiece having an opening formed axially therethrough from a first end to an opposing second end thereof and an inner tubular member configured to be slidably received within the opening of the mouthpiece. A sliding of the inner tubular member within the opening of the mouthpiece changes an axial length of the mouthpiece assembly to allow for the mouthpiece assembly to be coupled to a variety of different outer tubular members of differing axial lengths that are compatible for use with the mouthpiece assembly for forming the resulting vaporizer device.

According to an additional aspect of the present invention, at least one sealing element may be disposed between an inner surface of the mouthpiece defining the opening thereof and an outer surface of the inner tubular member when the inner tubular member is received within the opening of the mouthpiece, wherein the at least one sealing element is compressed radially between the inner surface of the mouthpiece and the outer surface of the inner tubular member.

The mouthpiece may be configured to be coupled to an outer tubular member forming a component of the vaporizer device. The at least one sealing element may be disposed around an outer surface of the mouthpiece, wherein the at least one sealing element is configured to be compressed radially between the outer surface of the mouthpiece and an inner surface of the outer tubular member when the mouthpiece is coupled to the outer tubular member. The outer tubular member may include a port formed therethrough, wherein the port is disposed axially between the mouthpiece and an end of the inner tubular member disposed exterior to the opening of the mouthpiece when the mouthpiece is coupled to the outer tubular member. The inner tubular member may be slidably adjustable to an axial position relative to the mouthpiece wherein an axial space is formed between an end of the inner tubular member disposed exterior to the opening of the mouthpiece and an end of the outer tubular member disposed opposite the mouthpiece when the mouthpiece is coupled to the outer tubular member. The outer tubular member forms a vapor collection chamber of the vaporizer device into which a heated vapor is drawn during use of the vaporizer device.

The mouthpiece assembly may further include an insert configured for insertion into the opening of the inner tubular member. The insert may include a helical portion for increasing a flow path length through the inner tubular member.

A method of method of assembling a vaporizer device is also disclosed. The method includes the steps of: providing a mouthpiece assembly comprising a mouthpiece having an opening formed axially therethrough from a first end to an opposing second end thereof and an inner tubular member slidably received within the opening of the mouthpiece; sliding the inner tubular member relative to the mouthpiece to adjust an axial length of the mouthpiece assembly; and coupling an outer tubular member to the mouthpiece.

According to additional aspects of the disclosed method, the method may further comprise a step of inserting an insert into an opening formed axially through the inner tubular member. The inner tubular member may be slid relative to the mouthpiece until an exposed length of the inner tubular member extending beyond an end of the mouthpiece is less than a length of an opening of the outer tubular member extending beyond the end of the mouthpiece.

The inner tubular member may be slid relative to the mouthpiece until a desired axial distance is present between an exposed end of the inner tubular member disposed exterior to the opening of the mouthpiece and an end of an opening of the outer tubular member. The coupling of the outer tubular member to the mouthpiece may include compressing a sealing element between the mouthpiece and the outer tubular member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to necessarily limit the scope of the present disclosure.

FIG. 2 is an elevational cross-sectional view of the mouthpiece assembly of FIG. 1 when adjusted to a first operational position for minimizing an operational axial length of the mouthpiece assembly;

FIG. 3 is an elevational cross-sectional view of the mouthpiece assembly of FIG. 1 when adjusted to a second operational position for maximizing an operational axial length of the mouthpiece assembly;

FIG. 4 is an exploded perspective view showing an insert configured for insertion into the mouthpiece assembly of FIG. 1;

FIG. 5 is an elevational cross-sectional view of the mouthpiece assembly of FIG. 1 when having the insert received therein;

FIG. 6 is a side elevational view of a relatively short vaporizer device utilizing the mouthpiece assembly of FIG. 1;

FIG. 7 is an elevational cross-sectional view of the vaporizer device of FIG. 6 as taken from the perspective of line 7-7 in FIG. 6;

FIG. 8 is a side elevational view of a relatively long vaporizer device utilizing the mouthpiece assembly of FIG. 1;

FIG. 9 is an elevational cross-sectional view of the vaporizer device of FIG. 8 as taken from the perspective of line 9-9 in FIG. 8.

DETAILED DESCRIPTION

Figure 1:
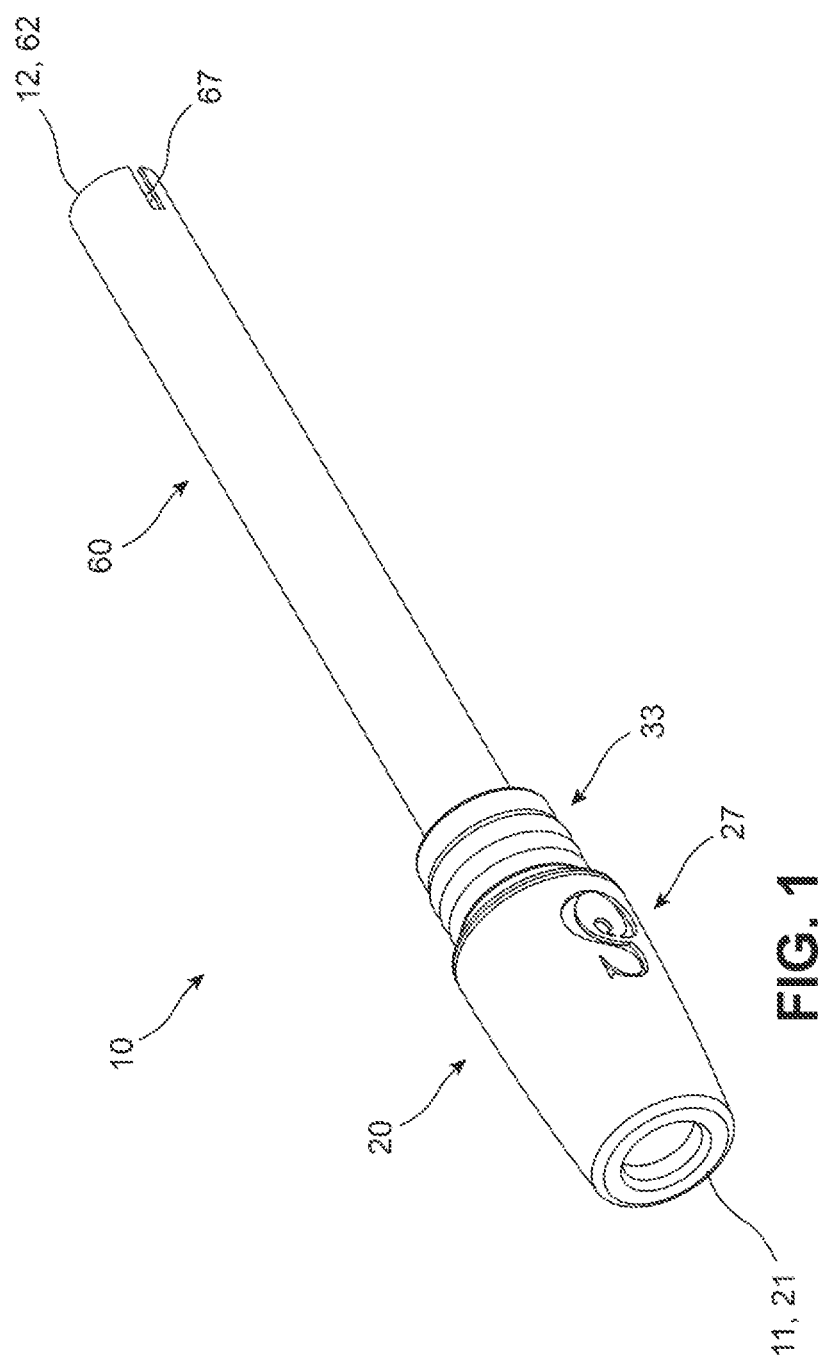
FIG. 1 is a perspective view of a mouthpiece assembly according to an embodiment of the present invention.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9,1-8,1-3,1-2,2-10, 2-8,2-3,3-10,3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

FIGS. 1-10 illustrate a mouthpiece assembly 10 according to an embodiment of the present invention. The mouthpiece assembly 10 forms a component of an associated vaporizer device. As explained in greater detail hereinafter, the mouthpiece assembly 10 includes an adjustable heat exchanging feature facilitating the use of the mouthpiece assembly 10 with any of a variety of different complimentary structures forming the associated vaporizer device. The mouthpiece assembly 10 as disclosed herein is accordingly not provided as a stand-alone product, but is instead configured for coupling to one of a variety of complimentary structures having varying shapes and configurations, thereby enhancing the versatility of the mouthpiece assembly 10 in providing a cooling effect to a vapor for a wide variety of different potential vaporizer device configurations.

Various aspects of the mouthpiece assembly 10 as well as the complimentary structure of the vaporizer device are described hereinafter as being tubular in configuration. As used herein, the term "tubular" does not necessarily refer to a cylindrical or other axially symmetric and hollow structure, but instead refers to any structure having a hollow opening elongated in an axial direction of the structure. For example, each of the components described hereinafter as being substantially cylindrical in shape may be replaced with corresponding components having a different closed polygonal cross-sectional shape, such as a square shape, a rectangular shape, a hexagonal shape, or the like, without departing from the scope of the present invention, so long as the resulting mouthpiece assembly 10 maintains the same general relationships described hereinafter. More specifically, such alternative cross-sectional shapes may be utilized so long as the mouthpiece assembly 10 maintains the same general flow configurations as described herein while also maintaining the ability to couple the mouthpiece assembly 10 to a corresponding complimentary structure for forming an exemplary vaporizer device. Further references to such axially symmetric features, such as cylindrical or annular shapes or surfaces, are accordingly not intended to be limiting to the scope of the present invention.

The mouthpiece assembly 10 comprises a mouthpiece 20 and an inner tubular member 60. In the provided embodiment, the mouthpiece 20 and the inner tubular member 60 are each substantially cylindrical in shape. The inner tubular member 60 is configured to be slidably received within the mouthpiece 20 for selectively adjusting an exposed length of the inner tubular member 60 disposed exterior to the mouthpiece 20. The inner tubular member 60 may alternatively be said to be telescopically received within the mouthpiece 20 due to the manner in which the sliding of the inner tubular member 60 relative to the mouthpiece 20 changes the axial length of the entirety of the mouthpiece assembly 10.

The mouthpiece 20 extends axially from a first end 21 to a second end 22, wherein the first end 21 of the mouthpiece 20 coincides with a first end 11 of the mouthpiece assembly 10. The mouthpiece 20 includes an inner surface 23 and an outer surface 24. The inner surface 23 defines an opening 25 extending axially through the mouthpiece from the first end 21 to the second end 22. In the illustrated embodiment, the opening 25 is shown as a substantially cylindrical bore.

The outer surface 24 of the mouthpiece 20 is divided axially into a piloting portion 27 and a coupling portion 33, each of which is substantially cylindrical in shape. The piloting portion 27 extends axially from the first end 21 of the mouthpiece 20 to a boundary between the piloting portion 27 and the coupling portion 33, while the coupling portion 33 extends axially from the boundary to the second end 22 of the mouthpiece 20. The piloting portion 27 of the outer surface 24 includes a tapered surface 28 and a radially extending surface 29. The tapered surface 28 may be provided to aid in piloting the mouthpiece 20 into a mouth of a user or into another adjacent component forming a portion of the associated vaporizer device, as desired.

The radially extending surface 29 connects the tapered surface 28 of the piloting portion 27 to an axially extending surface 34 of the coupling portion 33. In the illustrated embodiment, the radially extending surface 29 is annular in shape while the axially extending surface 34 is substantially cylindrical in shape. The coupling portion 33 includes a smaller radius/diameter than the tapered surface 28 at the intersection with the radially extending surface 29, causing the intersection of the tapered surface 28 and the radially extending surface 29 to form a stepped portion or shoulder on the outer surface 24 of the mouthpiece 20 at the transition from the piloting portion 27 to the coupling portion 33. The radially extending surface 29 is shown as being arranged substantially perpendicular to the central axis of the mouthpiece 20, but alternative angles of inclination may be utilized while remaining within the scope of the present invention.

The axially extending surface 34 of the coupling portion 33 includes a sealing indentation 35 formed therein. The sealing indentation 35 forms a radially inwardly indented portion of the coupling portion 33 relative to the adjacent segments of the axially extending surface 34. In the illustrated embodiment, the sealing indentation 35 further includes at least one seal receiving groove 36 formed therein, wherein each of the seal receiving grooves 36 is configured to receive at least a portion of a corresponding outer sealing element 38 therein. The mouthpiece assembly 10 is illustrated as including three axially spaced seal receiving grooves 36 with each of the seal receiving grooves 36 shaped to partially receive a corresponding outer sealing element 38 therein, but fewer or greater of the seal receiving grooves 36 and the corresponding outer sealing elements 38 may be utilized in the coupling portion 33 while remaining within the scope of the present invention. Each of the outer sealing elements 38 may be an annularly extending O-ring having a circular cross-section. However, the outer sealing elements 38 may have alternative cross-sectional shapes without necessarily departing from the scope of the present invention, and the seal receiving grooves 36 may also be modified to correspond in shape to the alternative shape of the outer sealing elements 38.

In all circumstances, the coupling portion 33 of the mouthpiece 20 is shaped and dimensioned to receive each of the outer sealing elements 38 therearound such that, prior to the coupling of the mouthpiece 20 to the inner tubular member 60, a first portion of each of the outer sealing elements 38 is disposed radially outwardly of the axially extending surface 34 and a second portion of each of the outer sealing elements 38 is disposed radially inwardly of the axially extending surface 34. This configuration ensures the ability to compress each of the outer sealing elements 38 radially inwardly to at least the radial position of the axially extending surface 34 upon the coupling of the mouthpiece assembly 10 to a corresponding complimentary structure. As such, each of the outer sealing elements 38 is formed from a resiliently flexible material which is configured to, when at room temperature, attempt to return to an original configuration thereof following elastic deformation. Each of the outer sealing elements 38 may be formed from an elastomeric material, such as a suitable rubber, as desired.

The inner surface 23 of the mouthpiece 20 similarly includes at least one seal receiving groove 41 formed therein, wherein each of the seal receiving grooves 41 is configured to receive a corresponding inner sealing element 42 therein. Each of the seal receiving grooves 41 forms a radially outwardly indented portion of the inner surface 23 relative to an axially extending surface 43 thereof. In the illustrated embodiment, the axially extending surface 43 includes a cylindrical contour. Each of the inner sealing elements 42 may be formed from a resiliently flexible material configured to, when at room temperature, attempt to return to an original configuration thereof following elastic deformation. Each of the inner sealing elements 42 may be formed from an elastomeric material, such as a suitable rubber, as desired. Each of the inner sealing elements 42 may be an O-ring having a circular cross-sectional shape, as desired.

The depth of each of the seal receiving grooves 41 with respect to the radial outward direction is selected to ensure that, prior to entry of the inner tubular member 60 into the opening 25 of the mouthpiece 20, a first portion of each of the inner sealing elements 42 is disposed radially inwardly of the axially extending surface 43 while a second portion of each of the inner sealing elements 42 is disposed radially inwardly of the axially extending surface 43. This configuration ensures the ability to compress each of the inner sealing elements 42 radially outwardly to at least the radial position of the axially extending surface 43 upon the coupling of the mouthpiece 20 to the inner tubular member 60. The radial compression of the inner sealing elements 42 aids in establishing a fixed position of the inner tubular member 60 relative to the mouthpiece 20 during use of the mouthpiece assembly 10.

In the illustrated embodiment, the at least one seal receiving groove 41 includes both a first seal receiving groove 41 disposed adjacent the second end 22 of the mouthpiece 20 and a second seal receiving groove 41 spaced axially from the first seal receiving groove 41 towards the first end 21 of the mouthpiece 20, wherein a corresponding inner sealing element 42 is disposed within each of the first seal receiving groove 41 and the second seal receiving groove 41. However, the mouthpiece assembly 10 may alternatively be provided with fewer or greater seal receiving grooves 41 and corresponding inner sealing elements 42, as desired, without necessarily departing from the scope of the present invention.

The inner surface 23 of the mouthpiece 20 further includes a radially extending surface 44 extending radially inwardly from an end of the axially extending surface 43 disposed adjacent the first end 21 of the mouthpiece 20. The radially extending surface 44 may extend radially a distance substantially corresponding to a radial thickness of the inner tubular member 60, but alternative radial distances may be utilized while remaining within the scope of the present invention. The radially extending surface 44 is positioned axially between the first end 21 of the mouthpiece 20 and the inner sealing element 42 disposed closest to the first end 21 with respect to the axial direction of the mouthpiece 20. The radially extending surface 44 is shown as being arranged substantially perpendicular to the central axis of the mouthpiece 20, but alternative angles of inclination may be utilized while remaining within the scope of the present invention.

The inner tubular member 60 extends axially from a first end 61 to an opposing second end 62, which also coincides with a second end 12 of the mouthpiece assembly 10. The inner tubular member 60 is shown as being substantially cylindrical in shape, thereby resulting in each of the first end 61 and the second end 62 being substantially annular in shape. The inner tubular member 60 includes an inner surface 63 and an outer surface 64. The inner surface 63 defines an opening 65 extending axially through the inner tubular member 60 from the first end 61 to the second end 62. In the illustrated embodiment, the opening 65 is shown as a cylindrical bore having a constant inner diameter along a length of the inner tubular member 60.

The outer surface 64 of the inner tubular member 60 includes a radius/diameter that is equal to or slightly smaller than a radius/diameter of the opening 25 along the axially extending surface 43, thereby facilitating axial insertion of the inner tubular member 60 into the opening 25 of the mouthpiece 20 at the second end 22 thereof. The radius/diameter of the outer surface 64 is also selected to be greater than a radius/diameter of the radially innermost end of the radially extending surface 44, thereby ensuring that the radially extending surface 44 of the mouthpiece 20 forms a stopping surface configured to engage the first end 61 of the inner tubular member 60 to establish an end axial position of the inner tubular member 60 relative to the mouthpiece 20. Once received within the opening 25 of the mouthpiece 20, the mouthpiece 20 and the inner tubular member 60 are concentrically arranged to have coinciding central longitudinal axes.

The inner tubular member 60 is shown throughout the figures as including a pair of diametrically opposing slots 67 formed therein. Each of the slots 67 penetrates the second end 62 of the inner tubular member 60 and extends rectilinearly in the axial direction of the inner tubular member 60 towards the first end 61.

The inner tubular member 60 is provided as a heat exchanging structure for exchanging heat energy with a vapor passing through the opening 65 of the inner tubular member 60. That is, the inner tubular member 60 provides additional surface area along which the previously heated vapor may exchange heat before reaching the user via the mouthpiece 20. Additionally, in some circumstances, the inner tubular member 60 may also provide for heat exchange between the inner tubular member 60 and a fluid or vapor passing around the outer surface 64 of the inner tubular member 60, such as when air is introduced into the vaporizer device exterior to the inner tubular member 60.

Referring now to FIGS. 4 and 5, the opening 65 of the inner tubular member 60 is further configured to axially receive an insert 80 therein for increasing the heat exchanging capacity of the mouthpiece assembly 10. The insert 80 extends longitudinally from a first end 81 to an opposing second end 82 thereof. The first end 81 forms a leading end of the insert 80 configured for initial entry into the opening 65 while the second end 82 of the insert 80 includes at least one laterally extending tab 83. Each of the laterally extending tabs 83 is configured to be received within one of the slots 67 formed in the second end 62 of the inner tubular member 60. The slots 67 accordingly allow for the insert 80 to be axially received into the inner tubular member 80 in a manner that does not cause the second end 82 of the insert 80 to extend axially beyond the second end 62 of the inner tubular member 60. This configuration can beneficially prevent any potential interference between the insert 80 and any components of the associated vaporizer device that may be disposed adjacent the second end 62 of the inner tubular member 60 when the mouthpiece assembly 10 is coupled to a compatible structure.

However, it should also be understood that the slots 67 are only an optional feature of the inner tubular member 60, and the inner tubular member 60 may operate in the absence of the slots 67. If such a configuration is utilized, the laterally extending tabs 83 of the insert 80 are instead caused to rest directly against the second end 62 of the inner tubular member 60 due to the laterally extending tabs 83 having a greater lateral length than the diameter of the inner tubular member 60. Either described configuration of the inner tubular member 60 may be utilized while remaining within the scope of the present invention.

The insert 80 further includes a helical portion 85 configured to form a helical flow path through the inner tubular member 60 when the insert 80 is received therein. The helical portion 85 disrupts laminar flow of a fluid or vapor passing through the inner tubular member 60 and can further introduce turbulence into the fluid or vapor, wherein it has been discovered that the introduction of such turbulence tends to increase the degree of heat exchange experienced by such a fluid or vapor when traversing the insert 85. The insert 85 also increases a fluid flow path length between the first end 61 and the second end 62 of the inner tubular member 60, which in turn increases the exposed surface area of the mouthpiece assembly 10 capable of exchanging heat energy with the fluid or vapor while also providing additional time for the heat exchange to occur for a given flow rate of the fluid or vapor.

The insert 80 is omitted from the remaining figures of the present patent application to better illustrate the features of the inner tubular member 60, but it should be understood that the insert 80 may be utilized in conjunction with the inner tubular member 60 with respect to any of the illustrated configurations of the mouthpiece assembly 10 or the resulting vaporizer device, as desired. It should also be understood that although the heat exchanging capacity is lowered, the inner tubular member 60 may still operate in the absence of the insert 80, as desired, without otherwise significantly altering the method of operation of the mouthpiece assembly 10.

Referring back to FIGS. 2 and 3, it can be seen that a telescoping of the inner tubular member 60 relative to the mouthpiece 20 results in a change in total axial length of the mouthpiece assembly 10 as measured between the opposing ends 11, 12 thereof. The inner tubular member 60 is configured to be adjustable relative to the mouthpiece 20 between a first operational position and a second operational position, wherein the adjustment occurs relative to the axial direction of the mouthpiece assembly 10.

The first operational position (FIG. 2) corresponds to a minimized operational length of the mouthpiece assembly 10 and a maximized axial overlap present between the mouthpiece 20 and the inner tubular member 60. The first operational position includes the first end 61 of the inner tubular member 60 abutting the radially extending surface 44 formed adjacent the first end 21 of the mouthpiece 20. The first operational position further includes each of the inner sealing elements 42 compressed radially between the outer surface 64 of the inner tubular member 60 and the inner surface 23 of the mouthpiece 20, thereby establishing a fluid tight seal therebetween.

In contrast, the second operational position (FIG. 3) corresponds to a maximized operational length of the mouthpiece assembly 10 that maintains the fluid tight seal between the inner surface 23 of the mouthpiece 20 and the outer surface 64 of the inner tubular member 60. The second operational position includes the first end 61 of the inner tubular member 60 spaced axially from the radially extending surface 44 of the mouthpiece 20 and disposed adjacent the inner sealing member 42 disposed closest to the first end 21 of the mouthpiece 20. The second operational position further includes each of the inner sealing elements 42 compressed radially between the outer surface 64 of the inner tubular member 60 and the inner surface 23 of the mouthpiece 20, thereby establishing the fluid tight seal therebetween.

The inner tubular member 60 is further adjustable to any number of axial positions relative to the mouthpiece 20 that are intermediate the first operational position and the second operational position. The total range of axial movement of the inner tubular member 42 relative to the mouthpiece 20 while maintaining the full sealing effect of the inner sealing members 42 is accordingly equal to the axial distance present between the radially extending surface 44 of the mouthpiece 20 and the closest of the inner sealing elements 42 to the radially extending surface 44.

The inner tubular member 60 may also be fully axially removed from the mouthpiece 20 to facilitate a cleaning of the inner tubular member 60, as desired. It should also be apparent that the mouthpiece assembly 10 may still be operational when only one of the illustrated inner sealing elements 42 is compressed as a result of the axial position of the inner tubular member 60 relative to the mouthpiece 20, but such a circumstance is generally undesirable due to the reduced sealing effect and possible degradation of any exposed inner sealing elements 42 within the mouthpiece 20.

Referring now FIGS. 6-9, the mouthpiece assembly 10 is shown as being coupled to one of two exemplary outer tubular members 200, 300 compatible for use with the mouthpiece assembly 10. Each of the outer tubular members 200, 300 forms a portion of a vaporizer device 100, 110 that is operable with the mouthpiece assembly 10. Each of the disclosed outer tubular members 200, 300 may be an independently provided component that is manufactured and/or sold independently of the mouthpiece assembly 10. In some circumstances, each of the outer tubular members 200, 300 may be representative of a removable component of a vaporizer device that is sized and dimensioned such that the corresponding outer tubular member 200, 300 is compatible for use with the mouthpiece assembly 10. For example, an existing vaporizer device may include a mouthpiece structure that is normally coupled to the corresponding outer tubular member 200, 300. The removal of the outer tubular member 200, 300 from the originally provided mouthpiece structure may accordingly facilitate the ability to couple the outer tubular member 200, 300 to the mouthpiece assembly 10 shown and described herein. In other circumstances, each of the outer tubular members 200, 300 may be a stand-alone, independently produced and sold component intended for use with interchangeable components such as the mouthpiece assembly 10.

Each of the outer tubular members 200, 300 is shown as providing what may be referred to as a vapor extraction chamber or a vapor collection chamber of the associated vaporizer device 100, 110. Such a chamber is utilized as a space for receiving and collecting a vapor following a heating thereof in an upstream arranged component of the associated vaporizer device 100, 110. The outer tubular members 200, 300 may also be representative of a portion of the associated vaporizer device 100, 110 that is grasped by the user's hand during manual operation of the associated vaporizer device 100, 110.

Referring now to FIGS. 6 and 7, the outer tubular member 200 includes an opening 203 extending axially therethrough from a first end 201 to an opposing second end 202 of the outer tubular member 200. The outer tubular member 200 includes an inner surface 211 defining the opening 203 and an oppositely arranged outer surface 212. As illustrated, the outer tubular member 200 is substantially cylindrical in shape, but alternative shapes may be utilized while remaining within the scope of the present invention, so long as the outer tubular member 200 is shaped and dimensioned for coupling to the mouthpiece 20.

The outer tubular member 200 is divided axially into a coupling portion 205 and a casing portion 206. The coupling portion 205 includes the first end 201 of the outer tubular member 200 while the casing portion 206 includes the second end 202 thereof. The coupling portion 205 forms an axially extending segment of the outer tubular member 200 extending around the coupling portion 33 of the mouthpiece 20 while the casing portion 206 extends rearwardly from the coupling portion 205 and surrounds at least a portion of the inner tubular member 60.

The coupling portion 205 is accordingly formed by an end portion of the outer tubular member 200 having an inner diameter along the inner surface 211 thereof that is equal to or slightly greater than an outer diameter of the axially extending surface 34 of the coupling portion 33 of the mouthpiece 20, and that further includes a complimentary cross-sectional shape to that of the coupling portion 33. The inner diameter of the inner surface 211 along the coupling portion 205 is also selected to ensure that each of the outer sealing elements 38 is compressed radially as a result of the reception of the coupling portion 205 of the outer tubular member 200 over the coupling portion 33 of the mouthpiece 20. The compression of the outer sealing elements 38 serves to provide a fluid tight seal and to prevent removal of the outer tubular member 200 from the mouthpiece 20 as a result of the frictional forces applied to the outer tubular member 200 by the resiliency of the outer sealing elements 38.

The casing portion 206 of the outer tubular member 200 is shown in FIGS. 6 and 7 as having substantially the same shape and configuration as the coupling portion 205 thereof. However, the illustrated casing portion 206 is merely exemplary in nature, as the inner surface 211 and the outer surface 212 of the outer tubular member 200 may have substantially any configuration along the casing portion 206 thereof so long as the desired flow paths are provided within the opening 203 of the outer tubular member 200. For example, in some circumstances, one or both of the inner surface 211 and the outer surface 212 may include a varying diameter along a length of the outer tubular member 200 or other irregular features for introducing a desired flow turbulence or other flow condition to a fluid or vapor passing through the outer tubular member 200. Still, in other embodiments, the outer surface 212 of the outer tubular member 200 may include features introduced therein for aiding in gripping the outer tubular member 200, as desired.

The second end 202 of the outer tubular member 200 is configured to receive a flow of a vaporized fluid therein during operational use of the mouthpiece assembly 10 and the corresponding vaporizer device 100. Although pictured as open ended, the second end 202 of the outer tubular member 200 may be configured for coupling to an associated component of the vaporizer device 100 having a power source, heating element, and a source of the substance to be vaporized. In other embodiments, such components may be incorporated directly into the structure of the outer tubular member 200 at the second end 202 thereof.

The outer tubular member 200 is further illustrated as including a port 220 formed therein, wherein the port 220 provides fluid communication between an ambient environment disposed exterior to the outer tubular member 200 and the opening 203 formed within the outer tubular member 200. The port 220 is intended as an inlet for air to be introduced into the opening 203 during the operational use of the vaporizer device 100 having the mouthpiece assembly 10. The port 220 is positioned intermediate the first end 201 and the second end 202 of the outer tubular member 200. As shown in FIG. 7, when the outer tubular member 200 is coupled to the mouthpiece 20, the port 220 is also positioned between the second end 22 of the mouthpiece 20 and the second end 62 of the inner tubular member 60. The port 220 is also positioned within the outer tubular member 200 such that a fluid flow path exists between the port 220 and the second end 202 of the outer tubular member 200 that does not include the associated fluid passing through the opening 65 of the inner tubular member 60.

FIG. 7 depicts the inner tubular member 60 as being in the first operational position wherein the length of the mouthpiece assembly 10 is minimized in order to accommodate the axial length of the outer tubular member 200 while providing for a mixing chamber 230 at the second end 202 of the outer tubular member 200. The mixing chamber 230 is formed by a portion of the opening 203 extending axially between the second end 62 of the inner tubular member 60 and the second end 202 of the outer tubular member 200. The mixing chamber 230 forms a space wherein air entering the outer tubular member 200 through the port 220 can mix with a heated and vaporized substance entering the outer tubular member 200 through the second end 202 thereof.

As can be seen from review of FIG. 7, an adjustment of the inner tubular member 60 away from the first operational position and towards the second operational position changes various aspects of the flow pattern formed within the vaporizer device 100. For example, a flow path between the port 220 and the mixing chamber 230 is lengthened, the mixing chamber 230 is shortened axially and decreased in volume, and the length of the flow path through the total length of the mouthpiece assembly 10 is increased. As such, the adjustability of the axial position of the inner tubular member 60 allows a user to prescribe a desired flow configuration of the associated fluids through the vaporizer device 100 during a vaping session.

It is also evident from FIG. 7 that the length of the outer tubular member 200 limits the possible positions of the inner tubular member 60 relative to the mouthpiece 20, as a full adjustment to the second operational position will result in the inner tubular member 60 extending beyond the second end 202 of the outer tubular member 200. The first operational position may accordingly be utilized when coupling the mouthpiece assembly 10 to a relatively short outer tubular member 200.

The vaporizer device 100 as shown and described herein may be assembled according to the following process steps. First, a user axially inserts the first end 61 of the inner tubular member 60 into the opening 25 of the mouthpiece 20 at the second end 22 thereof. Continued axial entry of the inner tubular member 60 eventually results in the radial compression of each of the inner sealing elements 42 until the second operational position of the inner tubular member 60 is reached. The user may then selectively adjust the axial position of the inner tubular member 60 between the first and second operational positions to attain a desired axial length of the mouthpiece assembly 10 compatible for use with the corresponding outer tubular member 200. The inner tubular member 60 may alternatively be adjusted to prescribe a desired flow configuration within the vaporizer device 100 by adjusting the length of various flow paths, as desired.

Once the inner tubular member 60 is adjusted to a desired axial position, the insert 80 may be axially inserted into the second end 62 of the inner tubular member 60. The insert 80 is inserted until the tabs 83 are received within the slots 67 or until the tabs 83 contact the second end 62 of the inner tubular member 60.

Next, following the insertion of the insert 80, the mouthpiece assembly 10 is coupled to the outer tubular member 200. More specifically, the coupling of the mouthpiece assembly 10 to the outer tubular member 200 includes the insertion of the coupling portion 33 of the mouthpiece 20 into the coupling portion 205 of the outer tubular member 200 such that each of the outer sealing elements 38 is compressed radially between the overlapping coupling portions 33, 205. The outer tubular member 200 is received axially until the first end 201 thereof abuts the radially extending surface 29 of the mouthpiece 20.

Once fully assembled, a method of operation of the vaporizer device 100 may occur as follows. First, a user can obstruct the port 220 of the outer tubular member 200 while drawing in a heated vapor from the second end 202 of the outer tubular member 200 in a direction towards the first end 21 of the mouthpiece 20. The drawing of the heated vapor may occur by the user inhaling and forming a suction pressure at the first end 21 of the mouthpiece 20 that draws any fluid contained within the vaporizer device 100 towards the first end 21. The heated vapor is accordingly allowed to flow into the opening 203 with the heated vapor first introduced into the mixing chamber 230 at the second end 202. Once a desired mass of heated vapor is drawn into the outer tubular member 200, the user can then unobstruct the port 220 while still maintaining the suction pressure at the first end 21 of the mouthpiece 20. The opening of the port 220 allows for fresh ambient air to be drawn through the port 220 and mixed with any heated vapors present within the vaporizer device 100. This can allow fluid/vapor and fluid/air to mix within the mixing chamber 230 where the air can effectively cool the vapor-air mixture as well as reduce an amount of fluid/vapor drawn through the vaporizer device 100. The entry of fresh air through the port 220 can also reduce draw resistance in the vaporizer cooling system device.

Once the port 220 is unobstructed, the fresh air drawn in through the port 220 by the low pressure condition can create a vortex around the inner tubular member 60 that results in turbulence and mixing of the fresh air and fluid/vapor being drawn into the vaporizer device 100 from the second end 202 of the outer tubular member 200. Where the vaporizer device 100 is configured with the mixing chamber 230, the vortex/turbulent air mixes and adds to a Venturi effect ultimately providing additional cooling to the fluid/vapor drawing through the vaporizer device 100 by the user. This mixing can also occur in a space between the outer tubular member 200 and an exposed portion of the inner tubular member 60. The vortex can then continue through the inner tubular member 60 as a result of the helically shaped insert 80 disposed therein. Heat is transferred to the insert 80 and the inner tubular member 60 as the fluid mixture passes therethrough, thereby cooling the fluid mixture.

Referring now to FIGS. 8 and 9, the outer tubular member 300 is substantially identical to the outer tubular member 200, except the outer tubular member 300 is shown as being about 20% longer with respect to the axial direction thereof. The outer tubular member 300 is shown in comparison to the outer tubular member 200 to illustrate the manner in which the adjustment of the inner tubular member 60 relative to the mouthpiece 20 can recreate similar flow conditions within outer tubular members 200, 300 of varying axial lengths. Specifically, although the inner tubular member 60 is adjusted to the second operational position thereof for maximizing the length of the mouthpiece assembly 10, a mixing chamber 330 formed within the outer tubular member 300 still has substantially the same axial length as the mixing chamber 230 of FIG. 7.

The adjustability of the axial position of the inner tubular member 60 relative to the mouthpiece 20 allows for the mouthpiece assembly 10 to be installed into any of a number of different complimentary outer tubular members 200, 300 without altering the method of operation of the resulting vaporizer device 100, 110. The inner tubular member 60 may be adjusted to the first operational position for minimizing the length of the mouthpiece assembly 10 when intended for installation into a relatively short outer tubular member or the inner tubular member 60 may be adjusted to the second operational position for maximizing the length of the mouthpiece assembly 10 for installation into a relatively long outer tubular member. The length of various fluid flow paths through the corresponding vaporizer device can also be adjusted for any given length of the compatible outer tubular member, hence the adjustment of the inner tubular member 60 further allows for the prescription of a desired flow configuration with respect to any compatible outer tubular member.

The adaptability of the mouthpiece assembly 10 is beneficial to a purchaser of the mouthpiece assembly 10 because the purchaser can buy a single combined mouthpiece and heat exchanging structure assembly that is in turn compatible with multiple other outer tubular members sold independently of the mouthpiece assembly 10, thereby reducing the total costs to the purchaser. For example, the structure of an already purchased vaporizer device corresponding to the mouthpiece and/or heat exchanging structure thereof may be removed from the associated outer tubular member and replaced with the mouthpiece assembly 10, thereby allowing for the purchaser to utilize a previous purchased vaporizer device while appreciating the improved heat exchange properties of the disclosed mouthpiece assembly 10. Alternatively, the purchaser may only need to purchase independently sold structures or assemblies corresponding to the disclosed outer tubular member and any associated components thereof (such as a heating element, vapor source, battery, etc.), wherein the mouthpiece assembly 10 is adjustable to be shared among a plurality of the outer tubular members.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

The invention claimed is:

1. A mouthpiece assembly for use with a vaporizer device, the mouthpiece assembly comprising:
   a mouthpiece having a first opening formed axially therethrough from a first end to an opposing second end of the mouthpiece;
   an inner tubular member configured to be slidably received within the first opening at the second end of the mouthpiece, the inner tubular member having a second opening formed axially therethrough from a first end to an opposing second end of the inner tubular member, wherein the first end of the inner tubular member is disposed within the first opening and the second end of the inner tubular member is disposed exterior to the first opening when the inner tubular member is slidably received within the first opening, wherein a sliding of the inner tubular member within the first opening changes an axial length of a first flow path through the mouthpiece assembly formed by cooperation of the first opening and the second opening and extending from the first end of the mouthpiece to the second end of the inner tubular member; and
   at least one first sealing element, each of the at least one sealing elements disposed between an inner surface of the mouthpiece defining the first opening thereof and an outer surface of the inner tubular member when the inner tubular member is received within the first opening, each of the at least one sealing elements extending annularly around the outer surface of the inner tubular member in a circumferential direction thereof to form an annular seal between the inner tubular member and the mouthpiece when the inner tubular member is slidably received within the first opening.

2. The mouthpiece assembly of claim 1, wherein each of the at least one sealing elements is compressed radially between the inner surface of the mouthpiece and the outer surface of the inner tubular member when the inner tubular member is received within the first opening.

3. The mouthpiece assembly of claim 1, wherein the mouthpiece is configured to be removably coupled to an outer tubular member forming a component of the vaporizer device.

4. The mouthpiece assembly of claim 3, wherein at least one second sealing element is disposed around an outer surface of the mouthpiece, wherein the at least one second sealing element is configured to be compressed radially between the outer surface of the mouthpiece and an inner surface of the outer tubular member when the mouthpiece is coupled to the outer tubular member.

5. The mouthpiece assembly of claim 3, wherein the outer tubular member includes a port formed therethrough, wherein the port is disposed axially between the mouthpiece and the second end of the inner tubular member disposed exterior to the first opening when the mouthpiece is coupled to the outer tubular member.

6. The mouthpiece assembly of claim 3, wherein the inner tubular member is slidably adjustable to an axial position relative to the mouthpiece wherein an axial space is formed between the second end of the inner tubular member disposed exterior to the first opening of the mouthpiece and an end of the outer tubular member disposed opposite the mouthpiece when the mouthpiece is coupled to the outer tubular member.

7. The mouthpiece assembly of claim 3, wherein the outer tubular member forms a vapor collection chamber of the vaporizer device into which a heated vapor is drawn during use of the vaporizer device.

8. The mouthpiece assembly of claim 3, wherein the outer tubular member extends axially from a first end to a second end, the first end of the outer tubular member configured to be coupled to the mouthpiece and the second end of the outer tubular member spaced apart from the mouthpiece and configured to be coupled to a component of the vaporizer device having a power source, a heating element, and a source of a substance to be vaporized, wherein the outer tubular member forms a vapor collection chamber of the vaporizer device into which a heated vapor is drawn during use of the vaporizer device, wherein the outer tubular member includes a port formed therethrough, wherein the port is disposed axially between the mouthpiece and the second end of the inner tubular member disposed exterior to the first opening when the mouthpiece is coupled to the outer tubular member, wherein the inner tubular member is slidably adjustable to an axial position relative to the mouthpiece wherein an axial space is formed between the second end of the inner tubular member disposed exterior to the first opening of the mouthpiece and the second end of the outer tubular member when the mouthpiece is coupled to the outer tubular member, wherein the axial space forms a mixing chamber wherein air entering the outer tubular member through the port mixes with the heated vapor drawn from the vaporizer device into the outer tubular member at the second end thereof.

9. The mouthpiece assembly of claim 8, wherein a second flow path through the mouthpiece assembly extends from the port to the second end of the inner tubular member along an outer surface of the inner tubular member outside of the first flow path, wherein a sliding of the inner tubular member within the first opening changes an axial length of the second flow path through the mouthpiece assembly.

10. The mouthpiece assembly of claim 9, wherein a sliding of the inner tubular member within the first opening changes an axial length of the axial space forming the mixing chamber.

11. The mouthpiece assembly of claim 1, further comprising an insert configured for axial insertion into the second opening of the inner tubular member, wherein the insert is configured to increase a flow path length of a fluid through the first flow path.

12. The mouthpiece assembly of claim 11, wherein the insert includes a helical portion configured to guide a fluid passing through the second opening and along the insert in a helical flow configuration for increasing a flow path length through the second opening of the inner tubular member.

13. A method of assembling a vaporizer device including the steps of:
providing a mouthpiece assembly comprising:
a mouthpiece having a first opening formed axially therethrough from a first end to an opposing second end of the mouthpiece, and
an inner tubular member configured to be slidably received within the first opening, the inner tubular member having a second opening formed axially therethrough from a first end to an opposing second end of the inner tubular member;
inserting the first end of the inner tubular member into the first opening at the second end of the mouthpiece;
sliding the inner tubular member axially relative to the mouthpiece to adjust an axial length of a first flow path through the mouthpiece assembly formed by cooperation of the first opening and the second opening and extending from the first end of the mouthpiece to the second end of the inner tubular member; and
coupling an outer tubular member to the mouthpiece.

14. The method of claim 13, further comprising a step of axially inserting an insert into the second opening, the insert configured to increase a flow path length of a fluid through the first flow path.

15. The method of claim 13, wherein the inner tubular member is slid relative to the mouthpiece until an exposed length of the inner tubular member extending beyond the second end of the mouthpiece is less than a length of a third opening of the outer tubular member extending beyond the end of the mouthpiece.

16. The method of claim 13, wherein the inner tubular member is slid relative to the mouthpiece until a desired axial distance is present between the second end of the inner tubular member disposed exterior to the first opening of the mouthpiece and an end of a third opening of the outer tubular member.

17. The method of claim 13, wherein the coupling of the outer tubular member to the mouthpiece includes compressing a sealing element between the mouthpiece and the outer tubular member.

* * * * *